United States Patent [19]

Beller et al.

[11] Patent Number: 5,516,932
[45] Date of Patent: May 14, 1996

[54] HALOGENATED CINNAMIC ACIDS AND ESTERS THEREOF, PROCESSES FOR THE PREPARATION THEREOF AND HALOGENATED ARYLDIAZONIUM SALTS

[75] Inventors: Matthias Beller, Niedernhausen; Hartmut Fischer, Hofheim; Laurent Weisse, Oberursel; Klaus Forstinger, Kelsterbach; Ralf Pfirmann, Griesheim; Heinz Strutz, Usingen, all of Germany

[73] Assignee: Hoechst Aktiengesellschaft, Germany

[21] Appl. No.: 178,089

[22] Filed: Jan. 6, 1994

[30] Foreign Application Priority Data

Jan. 7, 1993 [DE] Germany ............ 43 00 195.5

[51] Int. Cl.$^6$ .................. C07C 69/76
[52] U.S. Cl. .............. 560/104; 562/495; 562/443; 562/470; 560/38; 560/60
[58] Field of Search ............ 560/104, 38, 60; 562/443, 470, 495

[56] References Cited

U.S. PATENT DOCUMENTS 3,345,263  10/1967  Subbaratnam .
4,346,248  8/1982   Deavenport et al. .
5,093,515  3/1992   Kumai et al. .

FOREIGN PATENT DOCUMENTS 0509426  10/1992  European Pat. Off. .
2630727  1/1978   Germany .

OTHER PUBLICATIONS

CA. 108:108029 1988.
Chemical Abstracts, vol. 58, No. 3, 1963, abstract no. 2389g.
Chemical Abstracts, vol. 51, No. 12, 1957, abstract no. 8667a.
Chemical Abstracts, vol. 74, No. 25, 1971, abstract no. 139822r.
Chemical Abstracts, vol. 95, No. 5, 1981, abstract no. 42172m.
Tetrahedron, vol. 37, No. 1, 1981, pp. 31–36.

*Primary Examiner*—Paul J. Killos
*Attorney, Agent, or Firm*—Connolly & Hutz

[57] ABSTRACT

The present invention relates to compounds of the formula

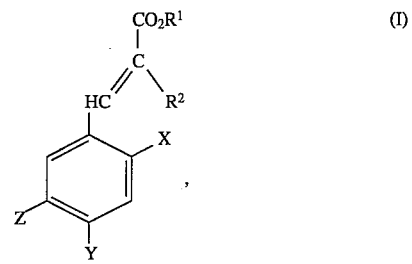

in which $R^1$ and $R^2$ are identical or different and are hydrogen or an alkyl radical having 1 to 18 carbon atoms and optionally containing oxygen, nitrogen or halogen, the radicals X, Y and Z are identical and are a fluorine, bromine or iodine atom or if two of the radicals X, Y or Z are identical or all of the radicals X, Y, Z are different from each other, X, Y and Z are a fluorine, chlorine, bromine or iodine atom. The invention further relates to a process for the preparation of the compounds, by reacting an aryldiazonium salt of the formula

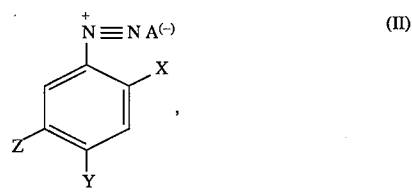

in which the radicals X, Y and Z are identical and are a fluorine, bromine or iodine atom or, if two of the radicals X, Y and Z are identical or all of the radicals X, Y, Z are different from each other, X, Y and Z are a fluorine, chlorine, bromine or iodine atom and $A^{(-)}$ is an anion of an acid having a $pK_a$ <7, with a compound of the formula

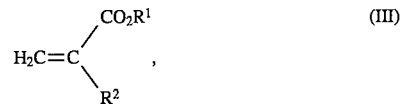

in which $R^1$ and $R^2$ are identical or different and are hydrogen or an alkyl radical having 1 to 18 carbon atoms and optionally containing oxygen, nitrogen or halogen, in the presence of a palladium-containing catalyst, if appropriate with addition of a base, and the aryldiazonium salts of the formula (II).

14 Claims, No Drawings

HALOGENATED CINNAMIC ACIDS AND ESTERS THEREOF, PROCESSES FOR THE PREPARATION THEREOF AND HALOGENATED ARYLDIAZONIUM SALTS

The present invention relates to novel halogenated cinnamic acids and esters thereof, processes for the preparation thereof and novel halogenated aryldiazonium compounds required for this.

Substituted cinnamic acids and cinnamic esters have industrial importance. They are used as materials absorbing ultraviolet light in creams, ointments and oils. In addition to their use as agents for light protection in the cosmetics sector, substituted cinnamic acids and esters thereof serve as odor substances and antioxidants (literature citations DE 3 139 994, DE 3 012 535, EP 484 122, U.S. Pat. No. 4 970 332, JP 04129790). Furthermore, they represent on the one hand valuable starting materials and intermediates for the preparation of herbicides, fungicides and pharmaceutically active substances and on the other hand themselves serve as active compounds, for example as lipoxygenase inhibitors or aldolase reductase inhibitors (JP 04193890, JP 04208211). The above areas of application also apply to the novel halogenated cinnamic acids and halogenated cinnamic esters.

Because of the general importance and versatile usability of this substance class, a worthwhile object is to provide novel compounds from this group of substances in order not only to supplement the spectrum of their potential applications but also to enrich and expand this by making subtle distinctions in material properties.

This object is achieved by compounds of the formula

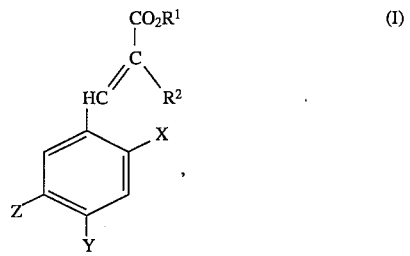

(I)

in which $R^1$ and $R^2$ are identical or different and are hydrogen or an alkyl radical having 1 to 18 carbon atoms and optionally containing oxygen, nitrogen or halogen, the radicals X, Y and Z are identical and are a fluorine, bromine or iodine atom or if two of the radicals X, Y or Z are identical or all of the radicals X, Y, Z are different from each other, X, Y and Z are a fluorine, chlorine, bromine or iodine atom.

Alkyl radicals which are generally suitable are cyclic, straight-chain or singly or multiply branched alkyl radicals which are saturated or monounsaturated or polyunsaturated and optionally contain one or more hetero atoms such as oxygen, nitrogen or a halogen. Examples of these radicals are methyl, ethyl, n-propyl, i-propyl, n-butyl, t-butyl, i-butyl, n-pentyl, i-pentyl, n-hexyl, i-hexyl, n-heptyl, i-heptyl, n-octyl, i-octyl, 2-ethylhexyl, nonyl, decyl, undecyl, dodecyl, tridecyl, tetradecyl, hexadecyl, octadecyl, 2-chloroethyl, 2-bromoethyl, 2-hydroxyethyl, 2-hydroxypropyl, 3-hydroxypropyl, 2-methoxyethyl, 2-ethoxyethyl, 4-ethoxybutyl, 2-propoxyethyl, 2-butoxyethyl, 3-methoxypropyl, 3-ethoxypropyl, 4-methoxybutyl, 3-ethoxybutyl, 3-hydroxypropyl, 4-hydroxybutyl, 3-chloropropyl, 2-chloropropyl, 2-acetoxyethyl, 3-acetoxypropyl, 4-acetoxybutyl, cyclopropyl, cyclobutyl, cyclopentyl, cyclohexyl, methylcyclohexyl, cycloheptyl, cyclooctyl, cyclodecyl, cyclododecyl, 2,3-epoxypropyl, 2-aminoethyl, 2-aminopropyl, 3-aminopropyl, 4-aminobutyl, 2-acetamidoethyl, 3-acetamidopropyl, 4-acetamidobutyl, 2-furyl, 3-furyl, 2-ethanyl, 2-propenyl, 2-butenyl, 3-butenyl, 2-hexenyl, 3-hexenyl, cyclopentenyl and cyclohexenyl.

$R^1$, apart from hydrogen, is an alkyl radical having 1 to 18, in particular 1 to 12, carbon atoms and optionally containing oxygen, nitrogen or halogen, in particular chlorine. These include straight-chain or branched alkyl radicals having 1 to 18, in particular 1 to 12, carbon atoms which are optionally substituted by an alkoxy group or an acyloxy group. The alkoxy groups or acyloxy groups can occupy any position. $R^1$ is in particular hydrogen or a methyl, ethyl, n-propyl, i-propyl, n-butyl, i-butyl, t-butyl, n-hexyl, i-hexyl, n-octyl, i-octyl, 2-ethylhexyl, decyl or dodecyl group.

The free cinnamic acids of the formula (I), in which $R^1$ is H, are of some importance since they themselves are of interest as intermediates for the above-stated applications and can be converted by reaction with alcohols into the corresponding esters and open the way to a multiplicity of esters.

Alkyl radical is also taken to mean radicals which are a $-(CH_2)_n-OR^3$ group, in which n=2 to 6 and $R^3$ is an alkyl radical having 1 to 4 carbon atoms, or a $-(CH_2-CH_2-O)_n-R^3$ group, in which n=2 to 4 and $R^3$ is an alkyl radical having 1 to 4 carbon atoms. This applies both to $R^1$ and to $R^2$, in particular $R^1$.

The compounds of the formula (I) in which $R^2$ is hydrogen or a methyl group are of interest. They can be simply and economically prepared.

In the event that X, Y and Z are identical, these radicals are each a fluorine, bromine or iodine atom. If two of the three radicals X, Y and Z are identical to each other, X, Y or Z are a fluorine, chlorine, bromine or iodine atom, in particular a fluorine, chlorine or bromine atom, the radicals identical to each other being in particular a fluorine or chlorine atom. If all of the radicals X, Y, Z are different from each other, X, Y and Z are a fluorine, chlorine, bromine or iodine atom, in particular a fluorine, chlorine or bromine atom.

Emphasis is to be placed on compounds of the formula (I), in which the two identical radicals X and Y are a bromine atom and Z is a fluorine atom or the two identical radicals Y and Z are each a fluorine atom and X is a bromine atom. In addition, compounds in which X is a bromine atom, Y is a chlorine atom and Z is a fluorine atom are also of importance.

Of particular importance are compounds of the formula (I), in which $R^1$ and $R^2$ are identical or different and are hydrogen or an alkyl radical having 1 to 18, in particular 1 to 12, carbon atoms and optionally containing oxygen, nitrogen or halogen, X is a chlorine atom and Y and Z are each a fluorine atom. Particular mention is to be made of compounds of this type in which $R^1$ is hydrogen or an alkyl radical, in particular a saturated alkyl radical having 1 to 12 carbon atoms, and $R^2$ is hydrogen or a methyl group, in particular hydrogen. Examples of these are the methyl, ethyl, n-propyl, i-propyl, n-butyl, i-butyl, t -butyl, pentyl, hexyl, octyl, 2-ethylhexyl, decyl, dodecyl, 2-chloroethyl, 2-aminoethyl, 2-acetamidoethyl, 2-acetoxyethyl and 3-acetoxypropyl esters of 2-chloro-4,5-difluorocinnamic acid. Preference is given to the methyl, ethyl, n-propyl, i-propyl, n-butyl, i-butyl, t-butyl, hexyl, octyl and 2 -ethylhexyl esters of 2-chloro-4,5-difluorocinnamic acid.

Of particular importance are likewise compounds of the formula (I), in which $R^1$ and $R^a$ are identical or different and are hydrogen or an alkyl radical having 1 to 18, in particular 1 to 12, carbon atoms and optionally containing oxygen, nitrogen or halogen and X, Y and Z are each a fluorine atom. Particular mention is to be made of compounds of this type in which $R^1$ is hydrogen or an alkyl radical, in particular a saturated alkyl radical having 1 to 12 carbon atoms, and $R^2$ is hydrogen or a methyl group, in particular hydrogen.

Examples of these are the methyl, ethyl, n-propyl, i-propyl, n-butyl, i-butyl, t-butyl, pentyl, hexyl, octyl, 2-ethylhexyl, decyl, dodecyl, 2-chloroethyl, 2-amino-ethyl, 2-acetamidoethyl, 2-acetoxyethyl and 3-acetoxypropyl esters of 2,4,5-trifluorocinnamic acid. Preference is given to the methyl, ethyl, n-propyl, i-propyl, n-butyl, i-butyl, t-butyl, hexyl, octyl and 2-ethylhexyl esters of 2,4,5-trifluorocinnamic acid.

Likewise of particular importance are compounds of the formula (I), in which $R^1$ and $R^2$ are identical or different and are hydrogen or an alkyl radical having 1 to 18, in particular 1 to 12, carbon atoms and optionally containing oxygen, nitrogen or halogen, X and Y are each a chlorine atom and Z is a fluorine atom. Particular mention is to be made of compounds of this type in which $R^1$ is hydrogen or an alkyl radical, in particular a saturated alkyl radical having 1 to 12 carbon atoms, and $R^2$ is hydrogen or a methyl group, in particular hydrogen. Examples of these are the methyl, ethyl, n-propyl, i-propyl, n-butyl, i-butyl, t-butyl, pentyl, hexyl, octyl, 2-ethylhexyl, decyl, dodecyl, 2-chloroethyl, 2-aminoethyl, 2-acetamidoethyl, 2-acetoxyethyl and 3-acetoxypropyl esters of 2,4-dichloro-5-fluorocinnamic acid.

Preference is given to the methyl, ethyl, n-propyl, i-propyl, n-butyl, i-butyl, t-butyl, hexyl, octyl and 2-ethylhexyl esters of 2,4-dichloro-5-fluorocinnamic acid.

In addition, compounds of the three groups mentioned above (1. X=Cl, Y=Z=F; 2. X=Y=Z=F; 3. X=Y=Cl; Z=F) are also of interest in which $R^1$ is a straight-chain or branched alkyl radical having 1 to 18, in particular 1 to 12, carbon atoms which are optionally substituted by an alkoxy or acyloxy group or a —$(CH_2)_n$—$OR^3$ group, in which n=2 to 6 and $R^3$ is an alkyl radical having 1 to 4 carbon atoms. $R^2$ is, in particular, hydrogen or a methyl group, preferably a hydrogen atom. Examples of these are the corresponding 2-hydroxyethyl, 2-methoxyethyl, 2-ethoxyethyl, 2-hydroxypropyl, 3-hydroxypropyl, 3-methoxypropyl, 3-ethoxypropyl, 4-methoxybutyl and 4-ethoxybutyl esters. Preference is given to the 2-hydroxyethyl, 2-methoxyethyl and 2-ethoxyethyl esters.

The halogenated cinnamic acids and esters thereof can be prepared by reacting a suitable olefinic compound, in particular an optionally substituted acrylic acid or an optionally substituted acrylic ester, with an appropriately substituted aryl halide, or an aryldiazonium compound, in the presence of a palladium-containing catalyst.

The aryldiazonium salts make possible a relatively simple preparation of the cinnamic acids and esters thereof. They are the subject-matter of the present invention and can be described by the formula

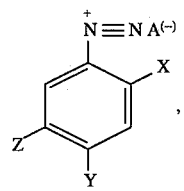
(II)

in which the radicals X, Y and Z are identical and are a fluorine, bromine or iodine atom, or, if two of the radicals X, Y and Z are identical or all of the radicals X, Y, Z are different from each other, X, Y and Z are a fluorine, chlorine, bromine or iodine atom and $A^{(-)}$ is an anion of an acid having a $pK_a<7$. Acids which can be used having a $pK_a<7$ are for example $HBF_4$, $HPF_6$, $H_2SO_4$, HCl, $HNO_3$, $CH_3COOH$, $H_3PO_4$, $HClO_4$, $CF_3COOH$, $CH_3CH_2COOH$, oxalic acid, $ClCH_2COOH$, $PhSO_3H$, $H_2SnCl_6$, in particular $HBF_4$, $HPF_6$, HCl, $H_2SO_4$, $CH_3COOH$, preferably $HBF_4$, $CH_3COOH$ or $H_2SO_4$.

Of particular importance are aryldiazonium compounds of the abovementioned formula (II), in which X is a chlorine atom and Y and Z are each a fluorine atom. Examples of these are 2-chloro-4,5-difluorophenyldiazonium tetrafluoroborate, 2-chloro-4,5-difluorophenyldiazonium hydrogen sulfate, 2-chloro-4,5-difluorophenyldiazonium sulfate, 2-chloro-4,5-difluorophenyldiazonium chloride, 2-chloro-4,5-difluorophenyldiazonium acetate, bis-(2-chloro-4,5-difluorophenyldiazonium) tin tetrachloride.

Likewise of particular importance are aryldiazonium compounds of the abovementioned formula (II), in which X, Y and Z are each a fluorine atom. Examples of these are 2,4,5-trifluorophenyldiazonium tetrafluoroborate, 2,4,5-trifluorophenyldiazonium hydrogen sulfate, 2,4,5-trifluorophenyldiazonium sulfate, 2,4,5-trifluorophenyldiazonium chloride, 2,4,5-trifluorophenyldiazonium acetate, bis-(2,4,5-trifluorophenyldiazonium) tin tetrachloride.

Equally of particular importance are aryldiazonium compounds of the abovementioned formula (II), in which X and Y are each a chlorine atom and Z is a fluorine atom. Examples of these are 2,4-dichloro-5-fluorophenyldiazonium tetrafluoroborate, 2,4-dichloro-5-fluorophenyldiazonium hydrogen sulfate, 2,4-dichloro-5-fluorophenyldiazonium sulfate, 2,4-dichloro-5-fluorophenyldiazonium chloride, 2,4-dichloro-5-fluorophenyldiazonium acetate, bis-(2,4-dichloro-5-fluorophenyldiazonium) tin tetrachloride.

The aryldiazonium compounds can be prepared by conventional methods (Houben Weyl, Methoden der organischen Chemie [Method of Organic Chemistry], Volume X/3, pages 3 to 214, in particular 12 to 113), by reacting an aromatic amine, appropriately substituted by halogen atoms, with nitrous acid, or a substance generating nitrous acid, for example alkali metal nitrite or another diazotizing substance, for example alkyl nitrite. This reaction does not pose any difficulties and generally leads to high yields. In many cases it is advisable to isolate the aryldiazonium salt and to further process it in a pure form, for example as a crystalline product. It is also possible to convert the diazonium salt prepared in solution directly into the particular cinnamic acids and cinnamic esters by palladium catalysts present in homogeneous form. If an alkali metal nitrite is employed, the preparation of the aryldiazonium compound becomes particularly favorable if at the same time an acid $H^+A^-$ is used in which $A^-$ is for example $BF_4^-$, $PF_6^-$, $HSO_3^-$, $Cl^-$, $H_2PO_4^-$, $ClO_4^-$ and $CH_3COO^-$ and in this manner the radical $A^-$ is already introduced into the aryldiazonium compound.

The preparation of cinnamic esters by a palladium-catalyzed reaction of an aryldiazonium salt with an acrylic acid derivative represents a process studied in more detail only recently.

K. Kikukawa et al., Chem. Lett., 1977, 159; Bull. Chem. Soc., 1979, 52, 2609 and Tetrahedron, 1981, 37, 31 describe the vinylation of aryldiazonium salts in the presence of soluble Pd(O) complexes and a base. The reactions only give good yields with the use of expensive bisbenzylidene palladium (O) in the presence of super-stoichiometric amounts of base. In addition, relatively high amounts (2 mol %) of palladium complex are used, which must be discarded after completion of the reaction. EP 0 508 264 describes a process for the preparation of substituted olefins from aryldiazonium salts and olefins in the presence of a palladium catalyst. The synthesis of cinnamic esters (Examples 20 to 22) is performed by Pd(OAc)$_2$ dissolved in the reaction mixture. The preparation of halogenated cinnamic acids and cinnamic esters is not mentioned in the above-mentioned prior art. The processes of the prior art have at any rate a considerable disadvantage. The palladium catalyst required for the reaction is used in homogeneous form, that is in the dissolved state. As a result, separation of the catalyst after the reaction is problematic. This is additionally made more difficult to a significant extent by the circumstance that the palladium catalyst is used in very small amounts, that is in the range from 0.1 to 5 mol %. A recovery of the valuable palladium catalyst and its reuse are not provided by the processes of the prior art, although this would be a desirable advantage for carrying out an industrial process.

Although the use of supported palladium catalysts is mentioned in EP-A 0 508 264 A1 page 4, lines 2 to 3, it is only referred to in one case, namely in the reaction of aniline-2-sulfonic acid with ethylene to give styrene-2-sulfonic acid (Example 6). However, as a comparison with Example 4 carried out using Pd(OAc)$_2$ shows, the yield decreases significantly when a palladium-containing supported catalyst (10% Pd on charcoal) is used (Example 4: 87% yield; Example 7: 74% yield). In both examples, the reaction is carried out using a base which is used in excess based on aniline-2-sulfonic acid. As the experimental findings prove (see comparative trial in the experimental part), the procedure practised in the examples of EP-A 0 508 264 to prepare the aryldiazonium salts in situ and then to further process them, cannot generally be applied to preparation of a cinnamic ester by a palladium-containing supported catalyst. The comparative trial verifies that the desired cinnamic ester is not even formed in small amounts. These experimental findings do not let it be expected that palladium-containing supported catalysts are suitable for the preparation of the cinnamic acids and cinnamic esters according to the invention.

The present invention further relates to a process for the preparation of the compounds according to the invention. It comprises reacting an aryldiazonium salt of the formula

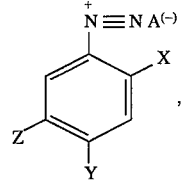
(II)

in which the radicals X, Y and Z are identical and are a fluorine, bromine or iodine atom or, if two of the radicals X, Y or Z are identical or all of the radicals X, Y, Z are different from each other, X, Y and Z are a fluorine, chlorine, bromine or iodine atom and A$^{(-)}$ is an anion of an acid having a pK$_a$<7, with a compound of the formula

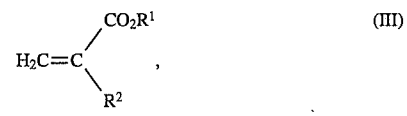
(III)

in which R$^1$ and R$^2$ are identical or different and are hydrogen or an alkyl radical having 1 to 18 carbon atoms which may contain oxygen, nitrogen or halogen, in the presence of a palladium-containing catalyst, if appropriate with addition of a base.

Aryldiazonium compounds of the formula (II), in which X is a chlorine atom and Y and Z are a fluorine atom, or X, Y and Z are each a fluorine atom or X and Y are each a chlorine atom and Z is a fluorine atom and A$^-$ is NO$_3^-$, BF$_4^-$, PF$_6^-$, HSO$_4^-$, Cl$^-$, CH$_3$COO$^-$, in particular BF$_4^-$, PF$_6^-$, HSO$_4^-$, Cl$^-$, CH$_3$COO$^-$, preferably BF$_4^-$ or HSO$_4^-$, are highly suitable for the process.

The process can be carried out both with palladium-containing catalysts in a homogeneous form, which are accordingly present in the dissolved state, and with palladium-containing catalysts in a heterogeneous form, in particular palladium-containing supported catalysts. Suitable homogeneous palladium compounds are for example palladium acetate, palladium dichloride, palladium dibromide, palladium dinitrate, sodium tetrachloropalladate and palladium sulfate. They can be used alone or in the form of any desired mixtures. In certain cases it can be advantageous in carrying out the process according to the invention to add compounds which form complexes with palladium or palladium salts. Suitable complexing agents are nitriles such as benzonitrile or acetonitrile and phosphites such as triethyl phosphite. Preference is given to phosphanes such as triarylphosphanes and trialkylphosphanes. It can also be advantageous to use chelating phosphanes or bisphosphanes or mixtures of bis- and monophosphanes. The phosphanes can be soluble in organic solvents and water, where in the last case these must be furnished with ionic substituents.

The palladium-phosphane complexes are preferably generated in situ, but preformed complexes, such as palladium tetrakisphenylphosphane can alternatively be used.

A particular advantage lies in the use of palladium-containing supported catalysts which can be separated off very easily, for example by filtration or decanting, after completion of the reaction. For an industrial process, arranging the palladium-containing supported catalyst in a fixed bed and passing the starting mixture to be converted over it is suitable. Separate application of the palladium-containing catalyst used as a fixed bed is no longer required.

Heterogeneous palladium catalysts are for example metallic palladium, palladium black or palladium fixed to a support material. The support materials which can be used are any desired inert solids. Examples which can be mentioned here are activated charcoal, aluminum oxides, silicon oxides, magnesium oxide, aluminosilicates, potassium carbonate, barium sulfate and calcium carbonate. Particularly suitable support materials are activated charcoal, aluminum oxides, silicon dioxides and aluminosilicates.

The reaction is conventionally carried out in the presence of a solvent. The solvents used can be both organic solvents, preferably dipolar aprotic solvents, and also protic solvents.

If the reaction is carried out in a dipolar aprotic solvent, the following solvents are suitable: ethers, preferably cyclic ethers such as tetrahydrofuran or dioxane and acyclic ethers such as methyl tert-butyl ether, glymes such as di-, tri- and tetraglymes, N,N-dialkylamides, particularly dimethylacetamide, dimethylformamide and N-methylpyrrolidone. Protic solvents which are suitable are alcohols, preferably methanol, ethanol, isopropanol, ethylene glycol, 2-ethylhexanol and water.

Mixtures of different solvents can also be used, even those which form multiple phase systems.

The process is conventionally carried out at a temperature from −10° to 120° C. In a number of cases, temperatures from 0 to 100, in particular 20° to 80° C., can be employed.

The present invention further relates to an additional process for the preparation of the above-described compounds. It comprises reacting an aryl halide of the formula

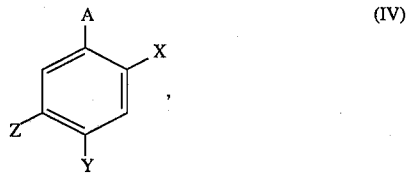

in which A is a bromine atom, X and/or Y is a fluorine atom or a chlorine atom and Z is a fluorine atom or A is a iodine atom, X-and/or Y is a fluorine atom, a chlorine atom or a bromine atom and Z is a fluorine atom or A is a chlorine atom, a bromine atom or an iodine atom and X, Y and Z are each a fluorine atom, with a compound

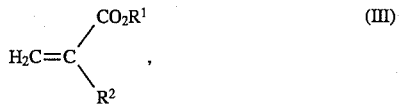

in which $R^1$ and $R^2$ are identical or different and are hydrogen or an alkyl radical having 1 to 18 carbon atoms which may contain oxygen, nitrogen or halogen, in the presence of a palladium-containing catalyst, if appropriate with addition of a base. The reaction can be carried out either without addition of a solvent or in the presence of a solvent. A solvent is conventionally used.

Suitable inert organic solvents, depending on the reaction components, are for example optionally chlorinated aliphatic, cycloaliphatic or aromatic hydrocarbons, such as n-pentane, n-heptane, n-octane, cyclopentane, cyclohexane, benzene, toluene, xylenes and chlorobenzene; aromatic, aliphatic and cyclic ethers, such as anisole, diethyl ether, diisopropyl ether, tetrahydrofuran and dioxane; N-substituted morpholines, such as N-methyl- and N-formylmorpholine; nitriles, particularly benzonitrile and alkylnitriles having 2 to 5 carbon atoms, such as acetonitrile, propionitrile, butyronitrile, 3-methoxypropionitrile and 3-ethoxypropionitrile; dialkyl sulfoxides, such as dimethyl sulfoxide and diethyl sulfoxide; N,N-dialkylamides of aliphatic monocarboxylic acids having 1 to 3 carbon atoms in the acid moiety, such as N,N-dimethylformamide and N,N-dimethylacetamide; alcohols having up to 8 carbon atoms, such as ethanol, n-propanol and tert-butanol; aliphatic and cyclic ketones, such as acetone, diethyl ketone, methyl isopropyl ketone, cyclopentanone, cyclohexanone, 1,3-dimethyl-2-imidazolidinone and 1,3-dimethyl-3,4,5,6-tetrahydro-2-(1H)-pyrimidinone; tetramethylurea; esters such as esters of carboxylic acids, for example diethyl carbonate; nitromethane$ alkyl esters or alkoxyalkyl esters of aliphatic monocarboxylic acids having in total 2 to 8 carbon atoms, such as methyl, ethyl, n-butyl and isobutyl acetates, ethyl and n-butyl butyrates and 1-acetoxy-2-ethoxyethane. Preferred solvents are N,N-dialkylamides, particularly dimethylacetamide, dimethylformamide, N-methylpyrrolidone and ethylene glycol dimethyl ether, di-, tri- and tetraethylene glycol dimethyl ether. Dipolar aprotic solvents are preferred as solvents.

Mixtures of the solvents can also be used, even those which form multiple phase systems.

It is advantageous to be able to react 2,4,5-trihaloaryl halides with acrylic acid or acrylic esters in the presence of bases.

Suitable bases are open-chain or cyclic secondary or tertiary amines, such as diethylamine, triethylamine, pyrrolidine, piperidine, piperazine, diazabicyclooctane (DABCO), diazabicyclonones (DBN), diazabicycloundecane (DBU), arylamines, aryldiamines, alkali metal salts and alkaline earth metal salts of aliphatic and aromatic carboxylic acids, such as sodium acetate, potassium acetate or calcium acetate, sodium propionate or potassium propionate, sodium laurate or potassium laurate, sodium benzoate or potassium benzoate, alkali metal carbonates and alkaline earth metal carbonates, such as potassium carbonate, sodium carbonate, lithium carbonate, calcium carbonate, alkali metal hydrogen carbonates and alkaline earth metal hydrogen carbonates, such as sodium hydrogen carbonate, calcium hydrogen carbonate or else alkali metal hydroxides or alkaline earth metal hydroxides, such as lithium hydroxide, potassium hydroxide, sodium hydroxide, calcium hydroxide and barium hydroxide. The bases mentioned can be used alone or in any mixtures with each other.

The reaction is expediently carried out at elevated temperature. Temperatures of 50° to 250° C. are conventionally employed. In most cases, a temperature of 60 to 200, in particular 80° to 180° C. has proven to be adequate for carrying out the reaction.

Suitable catalysts are palladium-containing catalysts both in homogeneous form and in heterogeneous form. Suitable homogeneous palladium compounds are palladium acetate, palladium dichloride, palladium dibromide, palladium dinitrate and palladium sulfate. They can be used alone or in any desired mixtures. In the reaction of the 2,4,5-trihaloaryl halides, it can be advantageous to add compounds which form complexes with palladium or with palladium salts. Suitable complexing agents are nitriles such as benzonitrile or acetonitrile and phosphites such as triethyl phosphite. Preference is given to phosphanes.

Monodentate monophosphanes which are suitable are in particular triarylphosphanes, dialkylarylphosphanes, diarylphosphanes, diarylalkylphosphanes and trialkylphosphanes, the alkyl groups containing 1 to 12 carbon atoms and the aryl groups being phenyl or naphthyl groups, each of which can be substituted by $C_{1-4}$-alkyl, $C_{1-3}$-alkoxy or $SO_3Na$.

Examples which can be mentioned are:

triphenylphosphane, tricyclohexylphosphane, triisopropylphosphane, tri-n-butylphosphane, tri(methoxyhenyl)phosphane, diisopropylphenylphosphane, diphenylisopropylphosphane, triisobutylphosphane, methyldiphenylphosphane, tri-o- and tri-p-tolylphosphane, triethylphosphane, tert-butyldiphenylphosphane and tri-(sulfonatophenyl)phosphane.

Particular preference is given to triphenylphosphane, tricyclohexylphosphane and tri-o-tolylphosphane.

It can also be advantageous to use chelating phosphanes or bisphosphanes or mixtures of bis- and monophosphanes. The phosphanes can be soluble in organic solvents and water, where in the last case these must be furnished with ionic substituents.

The palladium phosphane complexes are preferably generated in situ, but preformed complexes, such as palladium tetrakisphenylphosphane, can be alternatively used. Heterogeneous palladium catalysts are metallic palladium, palladium black or palladium fixed to a support material. The support materials which can be used are any desired inert solids. Examples which can be mentioned here are activated charcoal, aluminum oxides, silicon oxides, magnesium oxide, aluminosilicates, potassium carbonate, barium sulfate and calcium carbonate. Particularly suitable support materials are activated charcoal, aluminum oxides and silicon dioxides.

The amount of palladium used is expediently 0.001 to 10 mol %, preferably 0.01 to 5 mol %, based on the aryl halide.

The palladium content of the heterogeneous catalyst is 1 to 20% by weight, preferably 2 to 10% by weight, based on the support material.

The reaction can generally be carried out at reduced pressure, atmospheric pressure or superatmospheric pressure.

The examples below document the invention without restricting it thereto.

Experimental part

Comparative experiment (analogous to EP 0 508 264 Example 22)

12.3 g of 4-anisidine (4-methoxyaniline) are mixed with stirring with 10 ml of concentrated sulfuric acid and 60 ml of 2-ethylhexanol and the mixture is cooled to about 10° C. 11.7 g of amyl nitrite are then slowly added and the mixture is stirred for a further 40 minutes after addition is completed. 20.2 g of 2-ethylhexyl acrylate and 100 mg of Pd (5% by weight of Pd on activated charcoal) are then added to the reaction mixture which is heated in the course of 1 hour to 65° C. and stirred for 12 hours at this temperature. The mixture is diluted with 100 ml of water and extracted with 200 ml of dichloromethane. As studies by thin-layer chromatography and gas chromatography show, 2-ethylhexyl p-methoxycinnamate has not formed even in the smallest amounts. The 2-ethylhexyl acrylate used is present essentially in unchanged form.

EXAMPLE 1

8.78 g (31.5 mol) of 2,4-dichloro-5-fluorophenyldiazonium tetrafluoroborate and 11.61 g (63.0 mol) of 2-ethylhexyl acrylate are suspended in 40 ml of dimetyl sulfoxide and 0.75 g (0.32 mmol) of palladium (5% by weight of Pd on activated charcoal) are added at 0° C. The reaction mixture is heated to 60° C. in the course of one hour and stirred for 12 hours at this temperature. After cooling to room temperature, the catalyst is filtered off and washed with ethanol.

The mixture is diluted with 100 ml of dichloromethane and washed three times using 60 ml of water. The organic phase is concentrated in vacuo. The crude product produced is column-chromatographed.

Yield: 84% of 2-ethylhexyl 2,4-dichloro-5-fluorocinnamate.

$R_f$: 0.73 (ethyl acetate/petroleum ether 1:8).

Boiling point extrapolated from GC data: 363° C.

$^1$H-NMR (300 MHz, CDCl$_3$): 0.90, 0.92 (2 t, J=7.5 Hz, 6H, CH$_3$), 1.26–1.46 (m, 8H, CH$_2$), 1.57–1.70 (m, 1H, CH), 4.15 (dd, J=2, 7.5 Hz, 2H, CH$_2$O), 6.42 (d, J=16 Hz, 1H, CHCHCO2), 7.42 (d, J=9 Hz, 1H, CH), 7.47 (d, J=7 Hz, 1H, CH), 7.95 (dd, J=2, 16 Hz, 1H, CHCHCO$_2$).

$^{19}$F NMR (94 MHz): 116.9 (CF)

Mass spectrum (EI, 70 eV): 349 (38), 347 (63) (M+H), 219 (58), 217 (100) (C$_9$H$_4$OCl$_2$F), 112 (78) (C$_8$H$_{16}$).

EXAMPLE 2

The procedure of Example 1 is followed 1 mol % palladium based on diazonium salt (5% by weight on aluminum oxide) serves as the catalyst system.

Yield: 80% of 2-ethylhexyl 2,4-dichloro-5-fluorocinnamate.

EXAMPLE 3

8.78 g (31.5 mmol) of 2,4-dichloro-5-fluorophenyldiazonium tetrafluoroborate and 8.07 g (63.0 mmol) of butyl acrylate are suspended in 40 ml of dimethyl sulfoxide and 0.75 g (0.32 mmol) of palladium (5% by weight on activated charcoal) is added at 0° C. The reaction mixture is heated to 60° C. in the course of 1 hour and stirred for 12 hours at this temperature. After cooling to room temperature, the catalyst is filtered off and washed with ethanol.

The mixture is diluted with 100 ml of dichloromethane and washed three times using 60 ml of water. The organic phase is concentrated in vacuo. The crude product produced is column-chromatographed.

Yield: 73% of butyl 2,4-dichloro-5-fluorocinnamate.

$R_f$: 0.65 (ethyl acetate/petroleum ether 1.8).

Boiling point: 155°–160° C. at 0.8 mbar.

$^1$H-NMR (100 MHz, CDCl$_3$): 0.94 (t, J=7 Hz, 3H, CH$_3$), 1.22–1.82 (m, 4H, CH$_2$), 4.24 (t, J=7 Hz, 2H, CH$_2$O), 6.40 (d, J=16.5 Hz, 1H, CHCO$_2$), 7.43 (d, J=16.5 Hz, 1H, CH), 7.44 (s, 1H, CH), 7.93 (dd, J=2, 16.5 Hz, 1H, CHCHCO$_2$).

$^{19}$F-NMR (94 MHz): 117.0 (C-F)

EXAMPLE 4

8.78 g (31.5 mmol) of 2,4-dichloro-5-fluorophenyldiazonium tetrafluoroborate and 8.07 g (63.0 mmol) of ethyl acrylate are suspended in 40 ml of ethanol and 0.75 g (0.32 mmol) of palladium on activated charcoal (5% strength) is added at 0° C. The reaction mixture is heated to 60° C. in the course of 1 hour and stirred for 12 hours at this temperature.

After cooling to room temperature, the catalyst is filtered off and washed with ethanol.

The solvent is evaporated in vacuo. The crude product produced contains 87% of ethyl 2,4-dichloro-5-fluorocinnamate.

Yield: 93% of ethyl 2,4-dichloro-5-fluorocinnamate.

$R_f$: 0.59 (ethyl acetate/petroleum ether 1:8).

Boiling point: 147°–152° C. at 0.5 mm Hg. $^1$H-NMR (100 MHz, CDCl$_3$): 1.32 (t, J=7.5 Hz, 3H, CH$_3$), 4.28 (q, J=7.5 Hz, 2H, CH$_2$), 6.37 (d, J=16 Hz, 1H, CHCO$_2$), 7.40 (d, J=16.5 Hz, 1H, CH), 7.43 (s, 1H, CH), 7.91 (dd, J=2, 16 Hz, 1H, CHCHCO$_2$).

EXAMPLE 5

65.4 ml of butyl acrylate, 450 mg of palladium acetate, 1.075 g of triphenylphosphane, 0.815 g of bis(phenylphosphino)ethane and 20.15 g of sodium acetate are added to 50.0 g of 1-bromo-2,4-dichloro-5-fluorobenzene under protecting gas and the mixture is dissolved in 100 ml of dimethylacetamide. The reaction mixture is boiled for 12 hours at 140°–145° C. The mixture is then diluted with 200 ml of dichloromethane and washed twice by shaking with 100 ml of water. The organic phase is concentrated by a rotary evaporator.

Yield: 86% of butyl 2,4-dichloro-5-fluorocinnamate.

EXAMPLE 6

Synthesis of 2,4-dichloro-5-fluorophenyldiazonium tetrafluoroborate 165 ml of tetrahydrofuran are added to 100 g of 2,4-dichloro-5-fluoroaniline at room temperature. To this solution are added 333 ml of tetrafluoroboric acid (50% strength) with cooling. 57.5 g of sodium nitrite in 117 ml of water are added to the reaction mixture cooled to 5°–10° C. in such a way that the internal temperature is 7°–13° C. After addition is completed, the 0° C. solution is filtered. The residue is washed with tetrahydrofuran and ice-cold water. 121 g of product remain.

Yield: 80% of 2,4-dichloro-5-fluorophenyldiazonium tetrafluoroborate $^1$H-NMR (100 MHz, $D_2O$): 8.31 (d, J=6 Hz, 1H, CH), 8.65 (d, 6.5 Hz, 1H, CH)

$^{19}$F-NMR ($d_6$-acetone): 100.8 (t, CF), 151.3 (s, $BF_4$)

EXAMPLE 7

Alternative synthesis of 2,4-dichloro-5-fluorophenyldiazonium tetrafluoroborate 16 g of 2,4-dichloro-5-fluoroaniline are heated with 160 ml of tetrafluoroboric acid to 100° C. The orange-brown solution is then cooled to 0°–5° C. and 10.5 g of sodium nitrite in 25 ml of water are added dropwise. The reaction solution is then added to 200 ml of ice water. The product is removed by suction and washed with tetrahydrofuran.

Yield: 60% of 2,4-dichloro-5-fluorophenyldiazonium tetrafluoroborate.

EXAMPLE 8

Synthesis of ethylhexyl 2,4,5-trifluorocinnamate 3.0 g (14.2 mmol) of 1-bromo-2,4,5-trifluorobenzene are refluxed under protecting gas with 30.0 mmol of 2-ethylhexyl acrylate, 140 mg of palladium on activated charcoal (5% strength), 0.82 g of sodium carbonate and 10 mg of di-tert-butylphenol in 10 ml of dimethylacetamide for 18 hours at 170° C. The catalyst is filtered off, the mixture is diluted with dichloromethane and extracted with water. The crude product is chromatographed.

Yield: 87% of ethylhexyl 2,4,5-trifluorocinnemate $R_f$=(ethyl acetate/petroleum ether 1:6)

$^1$H-NMR ($CDCl_3$): 0.91, 0.93 (2 t, J=7.5 Hz, 6H, $CH_3$), 1.27–1.46 (m, 8H, $CH_2$), 1.59–1.72 (m, 1H, CH), 4.17 (dd, J=2, 7.5 Hz, 2H, $CH_2O$), 6.46 (d, J=16 Hz, 1H, CHC $\underline{H}CO_2$), 7.46–7.55 (m, 2H, CH), 7.99 (dd, J=2, 16 Hz, 1H, C$\underline{H}$CHCO$_2$).

MS (70 eV): 315 (100%) $M^+$

EXAMPLE 9

Synthesis of 2,4-dichloro-5-fluorophenyldiazonium hydrogen sulfate 36.0 g (0.20 mol) of 2,4-dichloro-5-fluoroaniline are dissolved at room temperature in 180 ml of ethanol and 36.0 g of concentrated sulfuric acid are added with cooling. To this mixture are added dropwise 27.0 ml (0.23 mol) of amyl 1 nitrite. The diazonium salt precipitated out is then removed by suction and washed with a little diethyl ether.

Yield: 74% of 2,4-dichloro-5-fluorophenyldiazonium hydrogen sulfate $^1$H-NMR (100 MHz, $d_6$-acetone): 8.83 (d, J=7 Hz, 1H, CH), 8.94 (d, J=7 Hz, 1 CH, CH)

We claim:

1. A compound of formula (I)

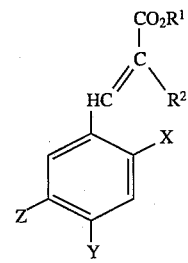

wherein

R$^1$ is a —(CH$_2$)$_n$—OR$^3$ group, in which n=2 to 6 and R$^3$ is an alkyl radical having 1 to 4 carbon atoms;

R$^2$ is the same as or different from R$^1$ and is hydrogen or an alkyl radical having 1 to 18 carbon atoms and optionally containing oxygen, nitrogen or halogen;

X, Y or Z are identical or all of the radicals X, Y and Z are different from each other, and X, Y and Z are a fluorine, chlorine, bromine or iodine atom.

2. A compound of the formula (I)

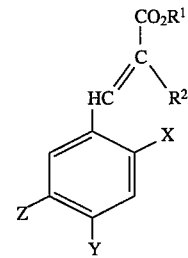

wherein

R$^1$ and R$^2$ are identical or different and are hydrogen or an alkyl radical having 1 to 18 carbon atoms and optionally containing oxygen, nitrogen or halogen; and X, Y and Z are as follows:
 (a) each of X and Y is a bromine atom and Z is a fluorine atom; or
 (b) X is a bromine atom, Y and Z are each a fluorine atom or Y is chlorine atom and Z is a fluorine atom; or
 (c) X is a chlorine atom, Y is bromine atom and Z is a fluorine atom; or
 (d) X and z are a fluorine atom and Y is a bromine or chlorine atom; or
 (e) X is a chlorine atom and Y and Z are each a fluorine atom; or
 (f) X, Y and Z are each a fluorine atom; or
 (g) X and Y are each a chlorine atom and Z is a fluorine atom.

3. A compound as claimed in claim 2, wherein X is a chlorine atom and Y and Z are each a fluorine atom, and wherein R$^2$ is hydrogen or a methyl group.

4. A compound as claimed in claim 2, wherein X is a chlorine atom and Y and Z are each a fluorine atom, and wherein R$^1$ is a straight-chain or branched alkyl radical having 1 to 18 carbon atoms and is optionally substituted by an alkoxy or acyloxy group.

5. A compound as claimed in claim 4, wherein the number of carbon atoms in said R$^1$ is 1 to 12.

6. A compound as claimed in claim 2, wherein X is a chlorine atom and Y and Z are each a fluorine atom, and wherein R$^l$ is a —(CH$_2$)$_n$—OR$^3$ group, in which n=2 to 6 and R$^3$ is an alkyl radical having 1 to 4 carbon atoms.

7. A process for the preparation of compounds as claimed in claim 1, which comprises reacting an aryl halide of the formula (IV)

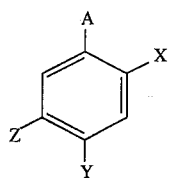

in which A is a bromine atom, and X, Y and Z are as defined in claim 1, with a compound of the formula III

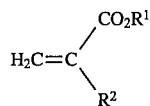

in which $R^1$ and $R^2$ are identical or different and are as defined in claim 1, in the presence of a palladium-containing catalyst, optionally with the addition of a base.

8. A process for the preparation of compounds as claimed in claim 2, which comprises reacting an aryl halide of the formula (IV)

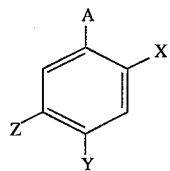

in which A is a bromine atom, and X, Y and Z are as defined in claim 2, with a compound of the formula (III)

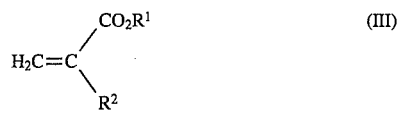

in which $R^1$ and $R^2$ are identical or different and are as defined in claim 2, in the presence of a palladium-containing catalyst, optionally with the addition of a base.

9. The process as claimed in claim 7, wherein the reaction is carried out in the presence of a solvent.

10. The process as claimed in claim 7, wherein the reaction is carried out in the presence of a dipolar aprotic solvent.

11. The process as claimed in claim 7, wherein the reaction is carried out at a temperature in the range of 50° to 250° C.

12. The process as claimed in claim 8, wherein the reaction is carried out in the presence of a solvent.

13. The process as claimed in claim 8, wherein the reaction is carried out in the presence of a dipolar aprotic solvent.

14. The process as claimed in claim 8, wherein the reaction is carried out at a temperature in the range of 50° to 250° C.

* * * * *

UNITED STATES PATENT AND TRADEMARK OFFICE
CERTIFICATE OF CORRECTION

PATENT NO. : 5,516,932
DATED : May 14, 1996
INVENTOR(S) : Matthias Beller, et al.

It is certified that error appears in the above-indentified patent and that said Letters Patent is hereby corrected as shown below:

In claim 2, at column 12, line 45, please delete the letter "z" and insert a --Z--.

In claim 6, at column 12, line 64, please delete the "R'" and insert --$R^1$--.

Signed and Sealed this

First Day of October, 1996

*Attest:*

BRUCE LEHMAN

*Attesting Officer*    *Commissioner of Patents and Trademarks*